United States Patent [19]

Rawls, Jr. et al.

[11] Patent Number: 5,709,223

[45] Date of Patent: Jan. 20, 1998

[54] MAGNETICALLY MODIFIED MICROBIAL METABOLISM

[75] Inventors: Walter C. Rawls, Jr., Jacksonville, Fla.; Gregory J. Provell, Somerset, N.J.

[73] Assignee: Bio Magnetics Systems, Inc., Newark, N.J.

[21] Appl. No.: 254,940

[22] Filed: Jun. 7, 1994

Related U.S. Application Data

[63] Continuation-in-part of Ser. No. 821,028, Jan. 15, 1992, Pat. No. 5,318,045, which is a continuation-in-part of Ser. No. 674,923, Mar. 26, 1991, Pat. No. 5,197,492, which is a continuation-in-part of Ser. No. 380,873, Jul. 17, 1989, Pat. No. 5,002,068.

[51] Int. Cl.[6] .................................................. A61B 19/00
[52] U.S. Cl. .................................................... 128/898
[58] Field of Search ........................... 128/898; 600/9–15

[56] References Cited

U.S. PATENT DOCUMENTS

| | | |
|---|---|---|
| 3,333,776 | 8/1967 | Elemi . |
| 3,664,327 | 5/1972 | Gordon et al. . |
| 3,921,620 | 11/1975 | Nakayama . |
| 4,020,590 | 5/1977 | Davis . |
| 4,134,935 | 1/1979 | Davis . |
| 4,602,359 | 7/1986 | Gordon . |
| 4,622,952 | 11/1986 | Gordon . |
| 4,622,953 | 11/1986 | Gordon . |
| 4,798,194 | 1/1989 | Amishime ........................ 600/15 |
| 5,017,185 | 5/1991 | Baermann ........................ 600/15 |
| 5,106,361 | 4/1992 | Liboff ............................. 600/13 |
| 5,123,898 | 6/1992 | Liboff ............................. 600/13 |

OTHER PUBLICATIONS

Magnetism and its Effects on the Living System Davis et al, Acres USA, Kansas City, Missouri, (1974).

The Magnetic Effect, Davis et al, Acres USA, Kansas City, Missouri, (1975).

Borstein et al, Argosy, Jun. (1968).

Evolving Perspective on the Exposure Risks from Magnetic Fields, A Trappier Journal of the National Medical Association, vol. 82, No. 9, pp. 621–624 Sep. 1990.

*Primary Examiner*—Michael A. Brown
*Attorney, Agent, or Firm*—Sheldon H. Parker

[57] ABSTRACT

This invention pertains to a method of modifying the reproduction rate of cells by exposing the cells to north directional unipolar magnetic fields, thereby decreasing the reproduction rate of the cells. The reproduction rate of the cells can also be modified by exposing them to south directional unipolar magnetic fields, thereby increasing the reproduction rate of the cells.

2 Claims, 7 Drawing Sheets

5,709,223

MAGNETICALLY MODIFIED MICROBIAL METABOLISM

CROSS-REFERENCE TO RELATED PATENT APPLICATIONS

This application is a continuation in part of Ser. No. 07/821,028 filed Jan. 15, 1992, now U.S. Pat. No. 5,318,045, which is a continuation-in-part of U.S. patent application Ser. No. 674,923, filed Mar. 26, 1991, now U.S. Pat. No. 5,197,492, which application is a continuation-in-part of U.S. patent application Ser. No. 380,873, filed Jul. 17, 1989, now U.S. Pat. No. 5,002,068, the subject matter of which is incorporated herein, in full, as though recited in detail.

FIELD OF THE INVENTION

This invention relates generally to methods for the modification of microbial metabolism using unipolar magnetic fields. In one aspect, this invention is directed to the modification of microbial metabolism, such as enhancing the microbial activity in the biodegradation of contaminated aqueous waste streams. In a further aspect, the present invention relates to methods for utilizing a unipolar magnetic field under controlled conditions to modify the metabolism of microorganisms.

BACKGROUND OF THE INVENTION

The search for a biological effect due to magnetic fields has a long history dating back a hundred years. The literature on biomagnetic effects on the growth and development of various organisms has been quite extensive showing both positive and negative findings. Among the positive findings attributed to strong magnetic fields are: altered growth rate, enzyme activities, cellular metabolism, DNA synthesis and animal orientation.

A wide variety of methods have been reported in the literature which are directed to the use of magnetic energy as a diagnostic technique and also for the treatment of diseases in warm blooded animals including humans. For example, magnetic energy has been utilized quite successfully over the past several years to promote the formation of osteoblasts in conjunction with the healing of bone fractures. In many instances markedly improved results in healing times have been achieved by the application of magnetic energy to the site of bone fractures and other injuries.

In U.S. Pat. No. 3,337,776, which issued Aug. 22, 1967, there is disclosed an apparatus for generating magnetic fields which are indicated to be particularly useful for biomedical applications. Although the patentee is not specific as to individual applications, he does state that magnetic fields generated by the apparatus can decrease metabolism and reacts on the spastic syndrome.

A magnetic probe is disclosed and claimed in U.S. Pat. No. 3,664,327 which issued May 23, 1972 and states that the probe can be employed in relatively inaccessible locations, such as in body cavities of animals to cause relaxation of muscle tissue.

A magnetic medical treatment device is disclosed in U.S. Pat. No. 3,921,620 which states that the effects of a magnetic field upon a living body is dissociated by polarization and induced currents and is effective in controlling the sympathetic nervous system.

On May 3, 1977, U.S. Pat. No. 4,020,590 issued to A. R. Davis discloses an apparatus and method for treating seeds in a unipolar magnetic field. It is indicated in the patent that this treatment enhances the germination rate of the seeds, as well as providing plants having greater sugar content, increased protein and other desirable features.

In U.S. Pat. No. 4,134,935 which issued Jan. 16, 1979 also to A. R. Davis, a method is disclosed and claimed which uses magnetic fields for clinical examination of animals to determine damaged, diseased, abnormal or malfunctioning parts of the body. Changes in tensioning and relaxation of the body extremities are an indication of body abnormalities.

A method for treating cancer is disclosed in U.S. Pat. No. 4,622,952 which issued Nov. 18, 1986 and which involves timing an electromagnetic energy to the resonant energy absorption frequencies of the intracellular structures of the selected cells. and then exposing a subject to this tuned electromagnetic energy field. The field can also be tuned to the frequency which has been calculated to be closest to the resonant frequency of the cancer cells and furthest from the normal cells.

U.S. Pat. No. 4,622,953, which issued to the same patentee, disclosed the identical procedure for the treatment of atherosclerotic lesions. In this process, metabolic and activity varying substance such as ferric hydroxide and dextran were employed and by applying the proper resonant energy, the heat in the diseased cell is increased by an increment sufficient to kill the diseased cell but not sufficient to kill normal cells.

In a patent issued to Robert T. Gordon on May 5, 1987, U.S. Pat. No. 4,602,359, a process is described and claimed for the treatment of cancer in a host organism which comprises providing to the host organism minute particles capable of being inductively heated and which are of a size which can be absorbed into cancer cells. Thereafter the organism is subjected to an alternating electromagnetic field to heat the particles at that point in metabolic time when the maximum difference in magnetic susceptibility between the cancer cells and normal cells within the region occurs, and then continuing the inductive heating to increase intracellular temperature to selectively kill the cancer cells.

Previous developments of directional magnetic fields began in 1936, when A. R. Davis first discovered that the north and the south magnetic pole fields each exhibited unique properties with respect to their effects on various forms of life. This discovery was slow to be accepted because of investigations by others who confused Davis' directional polarities magnetic fields with those which are simultaneously emitted by horse shoe type magnets and by AC-powered electromagnets. The common belief over the years relating to magnets has been that they emanate the same potential of type of energy. This belief has been found to be a misconception, since the two poles of a magnet are totally different in electric potential and effect. Correspondingly, the application of the respective poles to living systems has been found to produce quite different results. More specifically, it has been shown that magnetic energy has an effect on cells such as blood cells, nerves, bacteria, et al.

Preliminary investigations regarding biological effects of exposure to magnetic fields have indicated a polarity dependence. Cells are deemed to be bioelectric in nature, function and behavior and studies have indicated that directional magnetic fields enhance biological activity. Moreover, due to the orientation of such cells and of the metal elements and other ions contained therein, the blood cells have been found to decrease certain biological effects when exposed to the north pole and to increase other biological effects when exposed to the magnetic south pole. This same type of reaction has been noted in connection with other type cells of the body, it having been observed that, as a general matter, the application of north pole energies to an existing unhealthy or abnormal condition tends to have an arresting, quieting or relaxing effect, to induce an overall healing reaction akin to the body's own defense mechanism. On the other hand, the application of south pole energies tends to have a strengthening, activating effect, which has been found useful in treating some abnormal conditions, particularly those associated with a slowing or weakening in function. Cancer cells exposed to the north field show a significant decrease in the number of surviving cells after a period of incubation. Conversely, the same type of cells, when exposed to the south field, indicated an increase in the number of surviving cells compared to the unexposed controls. A more detailed description of magnetic pole energies can be found in Davis et al, Magnetism and its Effects on the Living System, Acres U.S.A., Kansas City, Mo. (1974) and Davis et al, The Magnetic Effect, Acres U.S.A., Kansas City, Mo. (1975).

The north pole, which is defined as the north seeking pole, is now believed to provide a negative form of energy while the south pole, which is defined as the south seeking pole, is believed to provide a positive form of energy. It has also been found upon examination of the electron paths associated with the fields surrounding the respective poles that the south pole end of a magnet provides a right hand spin of electrons, i.e., a clockwise rotation of electron movement, as contrasted with the north pole electron spin, which provides a left hand spin or counterclockwise rotation of its electron field.

It has been further observed that the lines of magnetic energy leave the south pole to re-enter the magnet at the Bloch Wall where the 180 degrees phase takes place, and leave the Bloch Wall at that point to go on as the north pole energy to re-enter the magnet at its north pole.

Magnetic enhancement or retardation of bacterial or cellular growth rates has been reported in the literature. For example, Davis and Rawls presented numerous examples of enhancement to seeds and various types of cellular growth (Davis, A. R. & Rawls, Jr., W. C., Magnetism and its Effects on the Living System, Acres, U.S.A., Kansas City, Mo., 1974). Bornstein reported magnetic inhibition of bacterial growth in burn wounds (Bornstein, L. A., in Argosy, June, 1968). Investigations sponsored by Bio-Magnetics Systems, Inc. have shown that unidirectional magnetic fields inhibited or increased the growth of cancer cells, depending on the field polarity, as disclosed by A. Trappier et al., in Evolving Perspectives On The Exposure Risks From Magnetic Fields, Journal of Nat. Med. Assoc., 82:621–624, September 1990.

SUMMARY OF THE INVENTION

In its broad aspect, this invention is directed to a method for the modification of microbial metabolism through the use of unipolar magnetic fields. In general, the method comprises exposing microbes to a unipolar magnetic field with gauss concentrations sufficient to effect microbial metabolism.

Bioremediation processes, in which microbes are used to repair ecological damage, are under development at the Environmental Protection Agency and elsewhere to treat a range of contaminants including aromatic solvents, polychlorobiphenyls, trichloroethylene, petroleum hydrocarbons and other organic constituents. The use of unipolar magnetic fields has the potential for enhancing the applicability and cost-effectiveness of bioremediation for the treatment of contaminated groundwater and contaminated soil. Specifically, it has now been found that the application of unipolar magnetic fields enhances microbial activity and will result in increasing the efficiency and rate of bioremediation, and proportionally decreasing the time required to meet cleanup goals. Thus, the unipolar magnetic field technology can save significant remediation costs at those toxic waste sites amenable to biological degradation. In addition, this technology can provide an integrated process for remediation. Such an integrated process can be based upon pump, treat, reinjection and/or direct application of magnetic field to the vadose zone to stimulate in situ biodegradation.

The method of modifying cells by exposing the cells to directional unipolar magnetic fields is also disclosed. The reproduction rate is increased when exposed to a south magnetic field, and decreased when exposed to a north magnetic field. The modification also applies to cells which derive energy for reproduction through fermentation. The modification can be either intracellular or modification is through the cell wall and the modification is retained within the cell.

Accordingly, one or more of the following objects will be achieved by the practice of this invention. It is an object of this invention to amplify or otherwise modify microbial metabolism and thereby enhance a process which employees microbes. These and other objects will readily become apparent to those skilled in the art in the light of the teachings therein set forth.

BRIEF DESCRIPTION OF THE DRAWINGS

The objects of the invention will become more apparent when the specification is read in conjunction with the drawings wherein.

DETAILED DESCRIPTION OF THE INVENTION

In its broad aspect, the present invention is directed to the modification of microbial metabolism by the application thereto of unipolar magnetic energy, i.e., the energy, north or south, emanating from a single pole of a magnet, under specific conditions to achieve the modification. The term modification is used herein to indicate an increase or decrease in the rate and/or efficiency of metabolism.

The biochemical processes of assimilation (anabolism) and dissimilation (catabolism) describe metabolism in microorganisms. Assimilation is the process by which organisms synthesize organic compounds from simple organic chemicals, $CO_2$, water, and other components. Dissimilation is the process by which organisms decompose organic compounds to CO2 and water, or partially decompose organics to lower molecular weight organics.

This invention modifies microbial metabolism using directional unipolar magnetic fields. Laboratory experiments have shown that south pole magnetic fields increase the rate of dissimilation in simulated bioremediation processes whereas north pole magnetic fields inhibit the rate of dissimilation (comparing to a control consisting of no magnetic fields).

Magnetically enhanced bioremediation is one area of application of the invention. Bioremediation is a process by which the use of living organisms, in conjunction with or independent from other technologies, is employed to decontaminate a polluted system. In bioremediation, contaminants are destroyed by the action of microbes such as soil bacteria.

Figure 1:
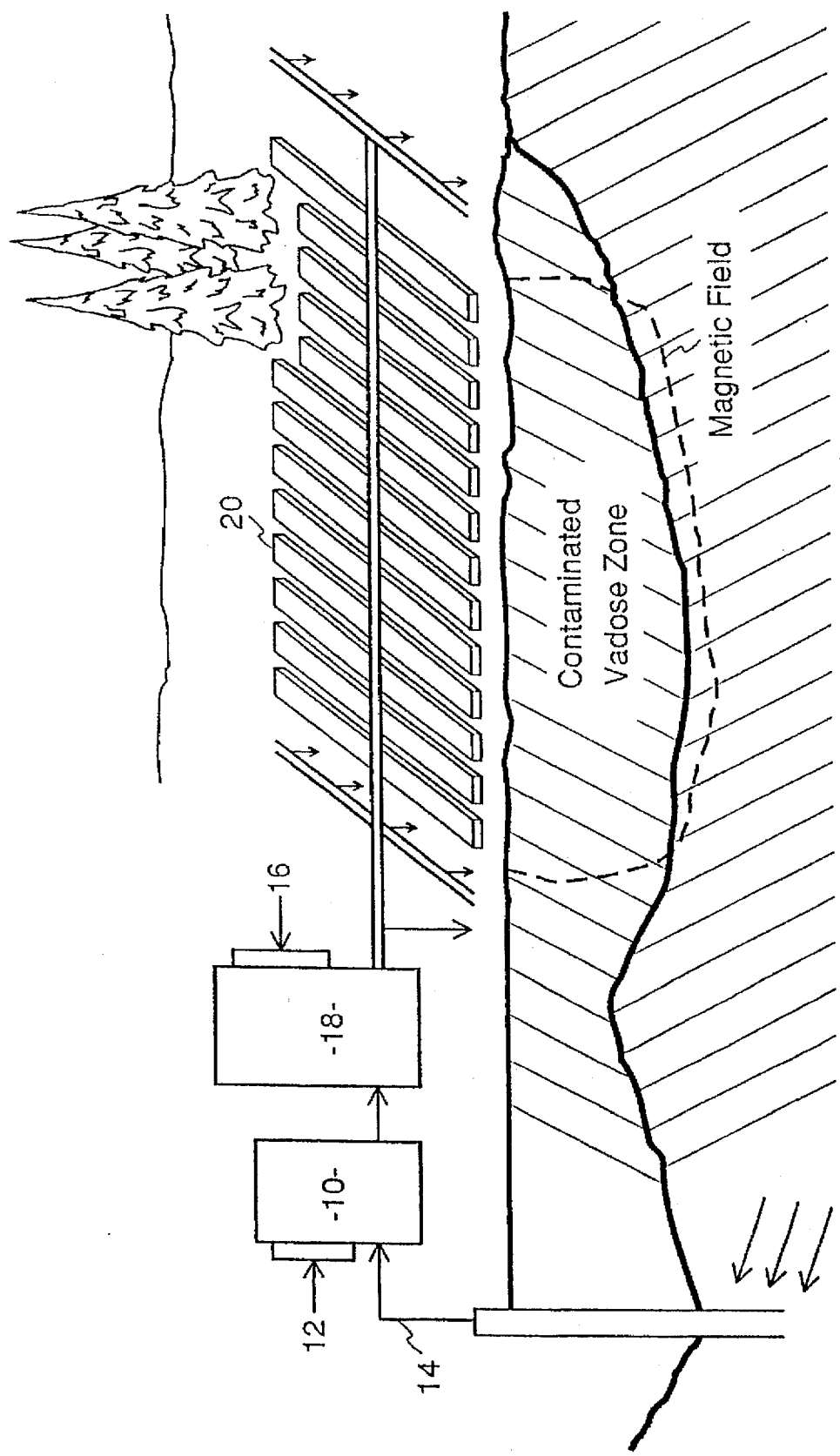
FIG. 1 is a schematic drawing of a toxic waste site showing an integrated approach for utilizing unipolar magnetic fields to modify the microbial activity in a bioremediation process.

FIG. 1 shows a schematic diagram of a toxic waste site showing an integrated approach for utilizing unipolar magnetic fields to modify the microbial activity in a bioremediation process. The unipolar magnetic field can be applied to the microbes before or after their contact with the toxic waste. Magnetically enhanced bioremediation is applicable to organic and inorganic wastes located in solid and aqueous media, including soil, slurries, sludges, and sediments. The process can use water as an intermediary to provide contact between magnetically enhanced bacteria and toxic waste substances. The presence of water in the soil as well as groundwater, itself, is compatible with magnetically enhanced bioremediation.

As shown in FIG. 1 a pretreatment reactor 10 can be provided with a magnet 12. A directional magnetic field is applied to the contaminated stream 14, in the reactor 10, by means of the magnet 12, which subjects the material in the pretreatment reactor to a south pole magnetic field. In the main reactor 18, microbes are added to the contaminated stream. A directional magnet 16 applies a south pole magnetic filed to the combined biomass in the main reactor 18. Optionally, nutrients are fed to the main reactor from a nutrient tank 11, or other source.

The oxidase and treated microbes are reinjected into the ground and is permitted to percolate into the ground. A magnetic blanket consisting of 9 inch wide, ¼ inch thick strips of pliable magnetic material 20, are laid over at least a portion of the field, thus subjecting the field to a south pole magnetic field.

A major advantage of this invention is that it can be used with existing bioremediation processes without introducing a major process modification or perturbation. The use of this invention could, however, result in the use of smaller, less costly process hardware and shorter operation times.

This invention can also be used to enhance biochemical processes in which microorganisms assist in producing chemicals such as plastics. For example, bacteria will make polymers, such as polyester under the proper conditions, and the use of unipolar magnetic fields will modify the rate and/or efficiency of this process.

Magnetically modified microbial metabolism would provide a basis for application to other governmental and commercial uses of microorganisms. Such uses can include any process where microorganisms such as bacteria are actively involved in a biochemical reaction.

The following examples are illustrative of the present invention.

EXAMPLE 1

Figure 2:
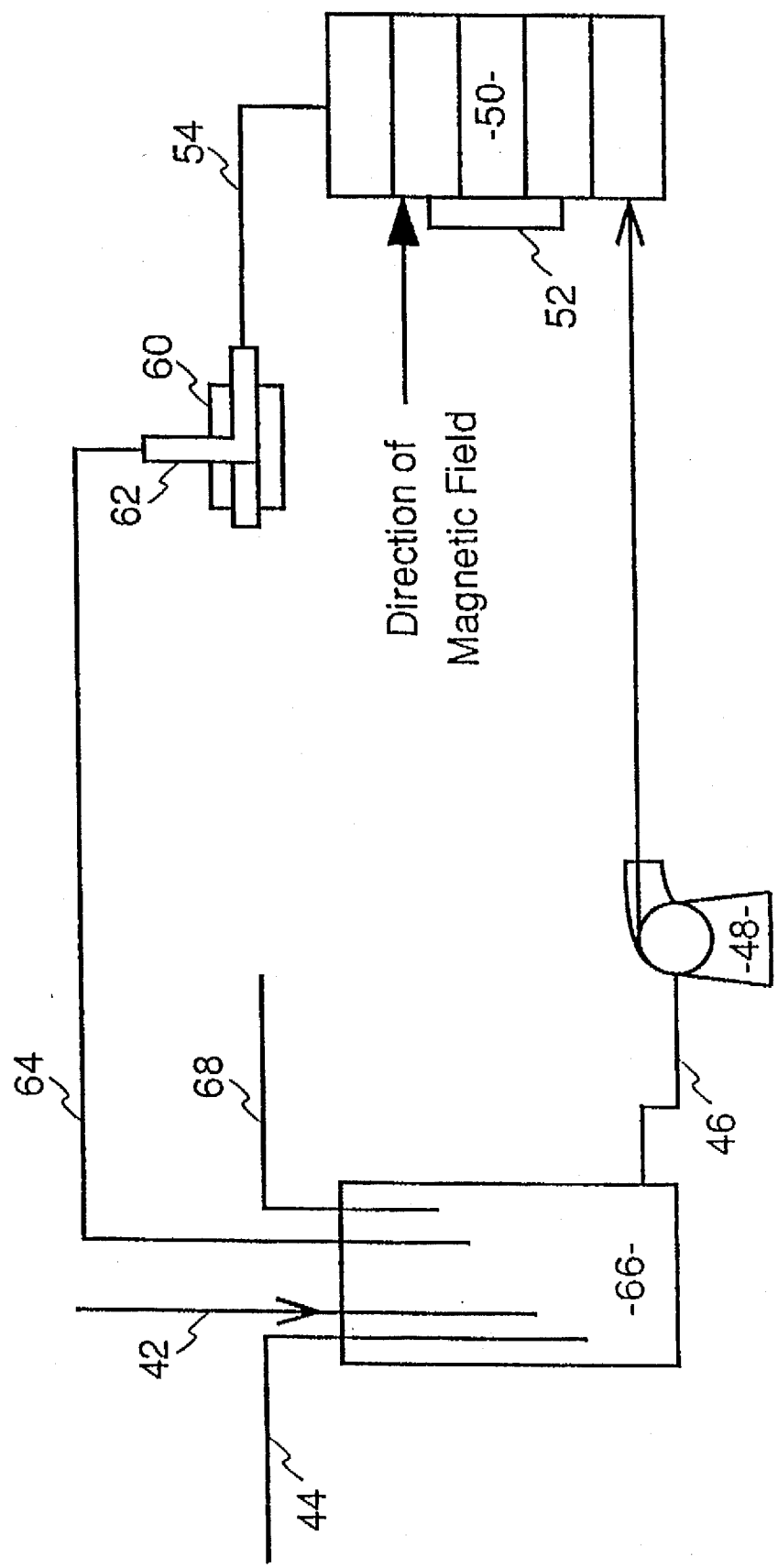
FIG. 2 is a drawing of a recirculating flow type biomagnetic reactor.

A recirculating flow type bioreactor was fabricated from nonmagnetic materials (plastics) and set-up as shown in FIG. 2. Solid state unipolar directional magnetic fields were applied to the reactor which contained 100 grams of alginate-immobilized, activated sludge prepared at the New Jersey Institute of Technology Biotechnology Laboratory, Newark, N.J. The bacterial culture in the sludge was immobilized in alginate matrix and activated by curing in 0.1 molar $CaCl_2$ solution. The magnetic field strength applied was varied. Air was continuously supplied as the source of dissolved oxygen. The oxygen consumption was monitored using a Clark-type dissolved oxygen probe and a strip chart recorder. Phenol was added to a mineral salt medium as the sole carbon source. It was constantly monitored for biodegradation in the experiment by sampling the reservoir and analyzing the samples in a Varian 3300 gas chromatograph. The concentration of secreted aeration in the medium, which continuously circulated between the reservoir and the reactor, was measured daily using the standard Lowery color response test. Each experimental run was 1200 hours (50 days) in length.

Runs performed were:
1. Control: no magnet on the bioreactor.
2. South magnetic pole exposure to the bioreactor.
3. North magnetic pole exposure to the bioreactor.
4. Changing the north magnetic pole exposure to a south magnetic pole exposure and the south magnetic pole exposure to a north magnetic pole exposure in the bioreactor.

Table 1 presents the results of these experiments. When the south pole magnetic energy was applied, biological oxidation rate was increased by a factor of two compared to the control run without magnetic energy present (from 0.656 to 1.545).

TABLE 1

| | Control | Directional South Pole | Directional North Pole g |
|---|---|---|---|
| Average rate of oxygen consumption (nmol/min ml) | 0.656 | 1.545 | 0.365 |
| Average secreted protein concentration (ug/ml) | 179 | 2422 | not detectable |
| Average rate of phenol biodegradation (ppm/hr) | 3.09 | 4.23 | 0.5 |

Figure 3:
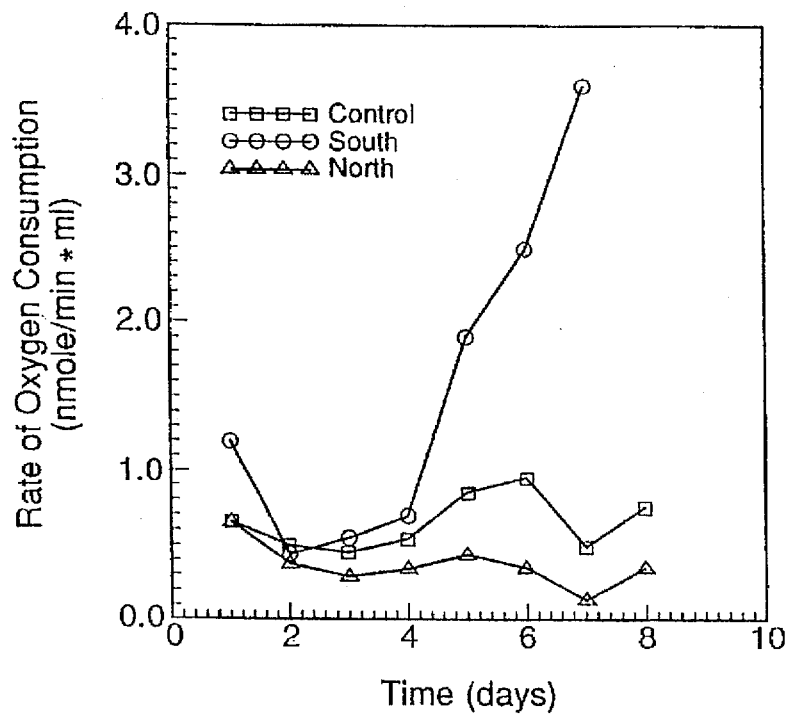
FIG. 3 is a graph showing the effect of unipolar magnetic fields on the rate of oxygen consumption in a bioreactor system.

FIG. 3 shows the effect of magnetic fields on the rate of oxygen consumption. It can be seen that the rate increased dramatically after 4 days of directional south pole magnetic field exposure as compared to north pole magnetic field exposure or control.

Results obtained from studies under the influence of north pole, south pole and during the control run are tabulated in Table 1. It can be seen that the highest average rate of phenol biodegradation and oxygen consumption is found during the run when south pole is attached to the bioreactor. When the magnetic south pole was applied, it increased the biological oxidation activity (oxygen consumption rate) by a factor of two as compared to the control run without magnetic field (from 0.7 to 1.5). FIG. 3 shows the effect of magnetic field on the rate of $O_2$ consumption. It can be seen that the rate increases dramatically after 4 days under the influence of south pole as compared to the control and north. One of the measures of biodegradation is the increase in activity that is the rate of oxygen consumption by the microbes in presence of a substrate like phenol. An increase in oxygen consumption indicates that it is being utilized by the microorganisms to break down phenol into its metabolic products which ultimately are $CO_2$ and water.

The phenol consumption rate is faster by nearly 30% in case of the run with the south pole as compared to the control run.

Figure 4:
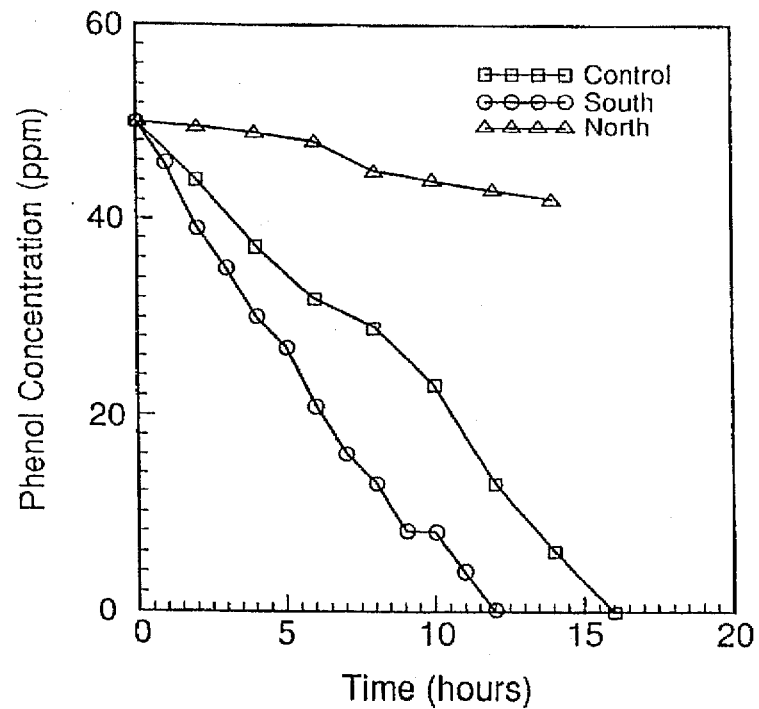
FIG. 4 is a graph showing the effect of unipolar magnetic fields on the rate of phenol consumption in a bioreactor system.

FIG. 4 indicates that the phenol concentration goes down rapidly under the influence of south pole comparison to the north pole and the control. These observations are consistent with those from the rate of oxygen consumption monitoring.

Figure 5:
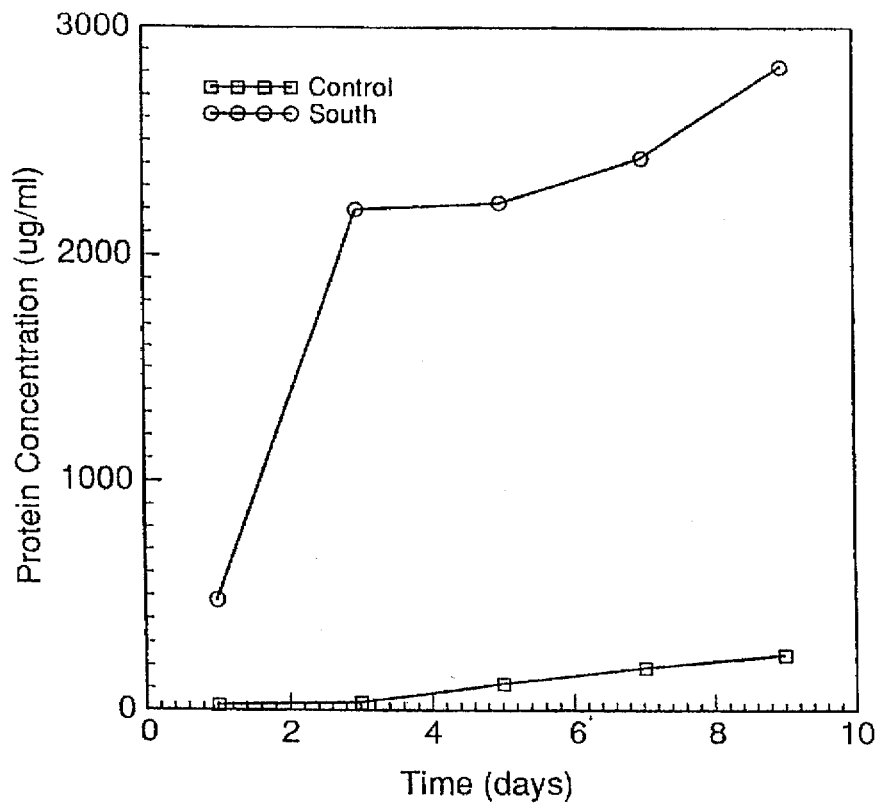
FIG. 5 is a graph showing the effect of unipolar magnetic fields on protein concentration in a bioreactor system.

Significant amounts of protein build-up in the liquid phase verified that biological activity was enhanced when magnetic south pole was applied to the system as compared to the control as shown in FIG. 5. Microorganisms release enzymes extracellularly which in turn attack the substrate. A higher amount of proteins in the reaction medium is a positive measure of biodegradation. FIG. 5 indicates that the south pole magnetic field greatly enhanced the concentration of protein in this reactor (protein is produced from phenol degradation). In this experiment it was observed that the pH changed from 7.9 to 8.5.

Figure 6:
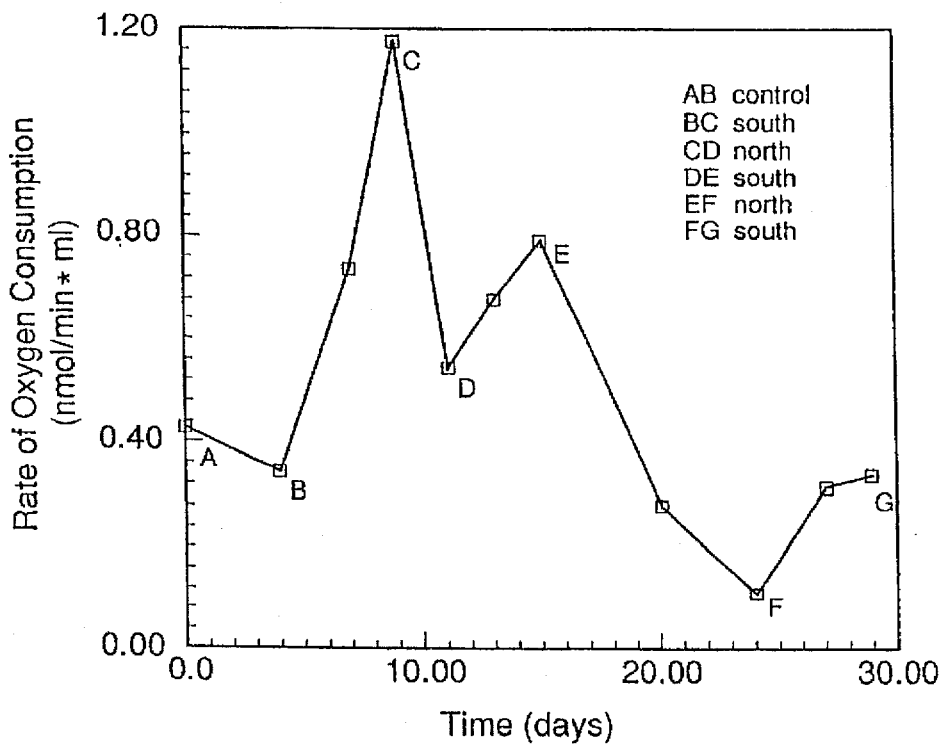
FIG. 6 is a graph showing the effect of reversing unipolar magnetic fields on the rate of oxygen consumption in a bioreactor system.

FIG. 6 shows the effect of repeatedly changing the south pole magnetic field to a north pole magnetic field and a north pole magnetic field to a south pole magnetic field in the bioreactor. The south pole field was consistently activating whereas the north pole field was inhibitory.

Figure 7:
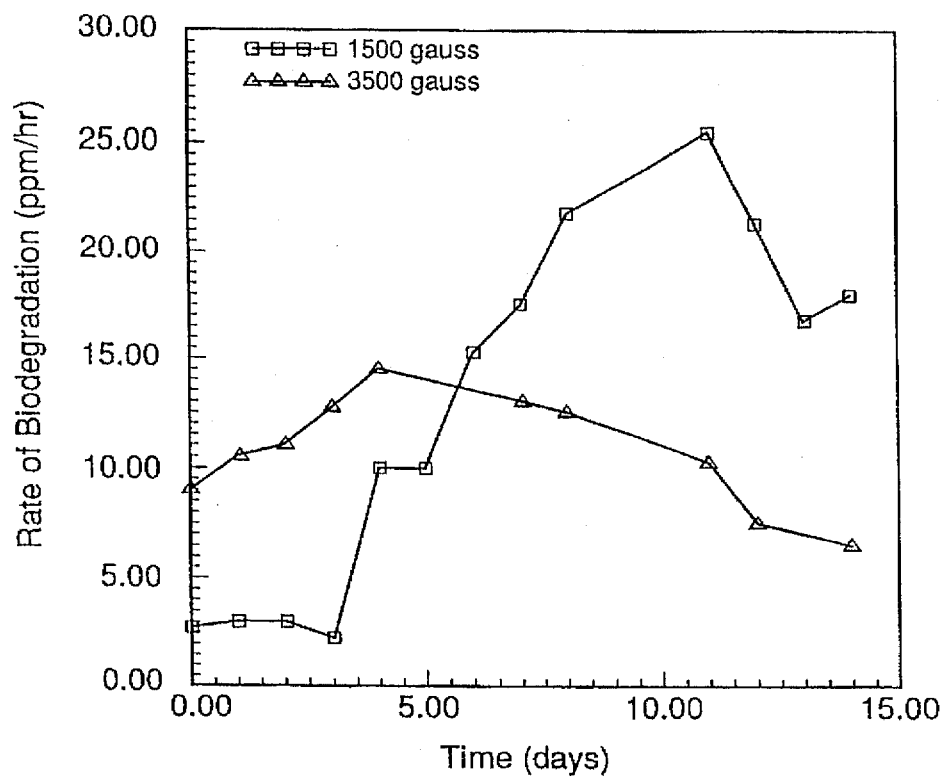
FIG. 7 is a graph which shows the effect on rate of biodegradation utilizing of different gauss strengths
Figure 8:
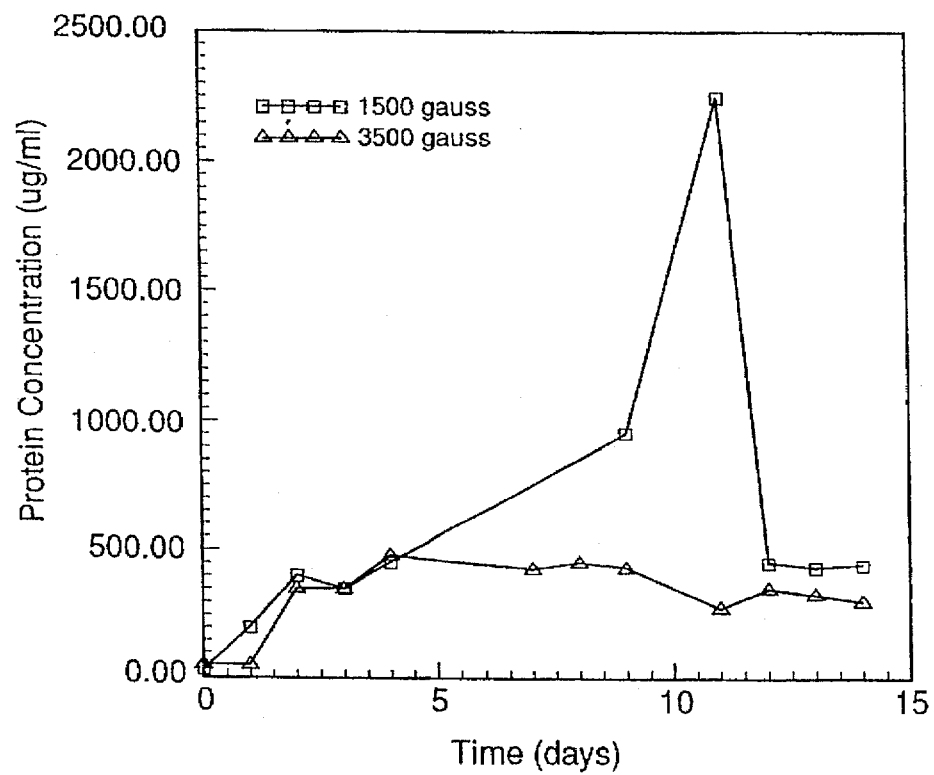
FIG. 8 is a graph which shows the effect on protein concentration utilizing different gauss strengths.

FIG. 7 and 8 show the effect of magnetic field on the rate of biodegradation and protein concentration under 1500 and 3500 gauss magnetic south pole. The highest rate of biodegradation is 25.6 ppm/h and the highest protein concentration8s 2250 ug/ml after 11 days under 1500 gauss.

Figure 9:
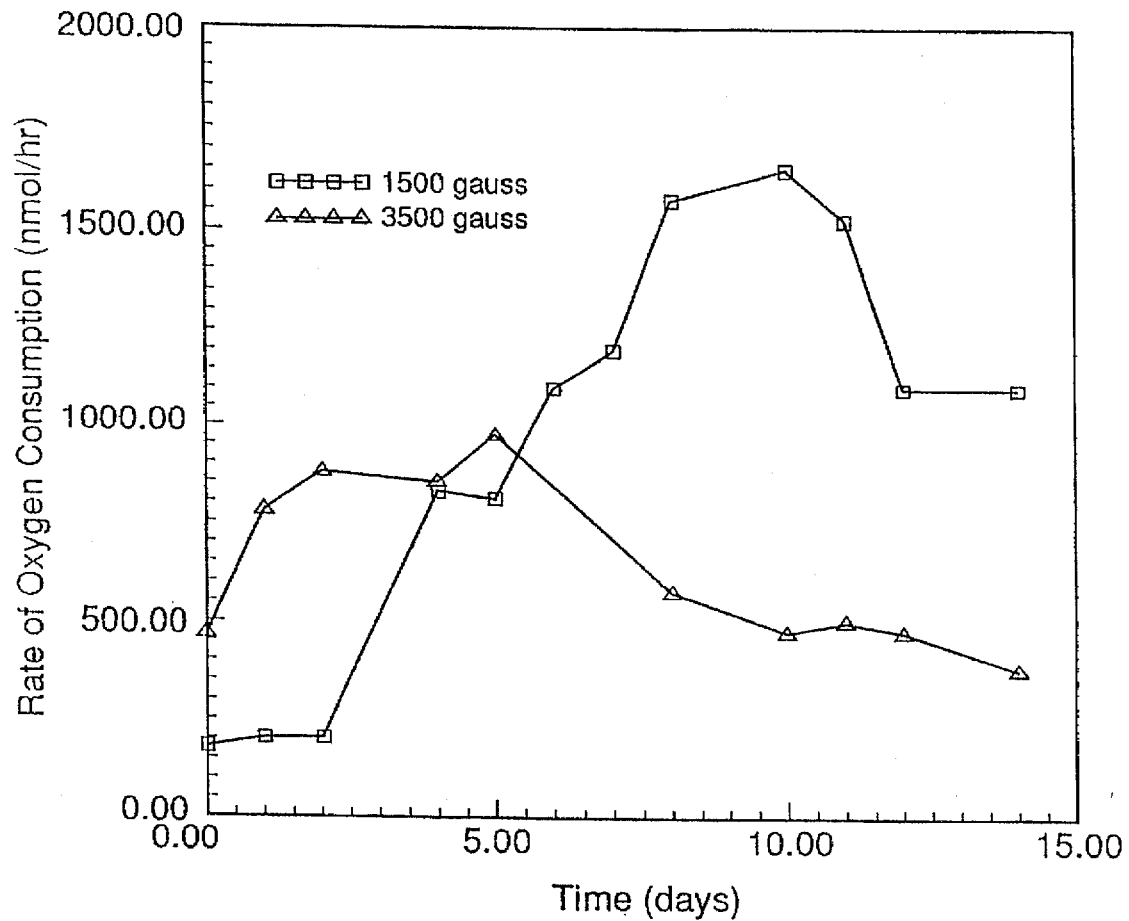
FIG. 9 is a graph which shows the effect on rate of $O_2$ consumption utilizing different gauss strengths.

FIG. 9 shows the effect of magnetic field on the rate of O2 consumption. It indicates that the highest rate of O2 consumption is 1649 nmol/ml*hr after 10 days under the influence of 1500 gauss magnetic south pole.

TABLE 2

Effects of acclimation on the rate of biodegradation

| Description | Rate of biodegradation (ppm/hr) |
| --- | --- |
| without magnet and unacclimated | 4.25 |
| without magnet after magnetic acclimation | 8.96 |
| with magnet (1500 gauss) after magnetic acclimation | 25.6 |
| with magnet (3500 gauss) after magnetic acclimation | 14.4 |

EXAMPLE 2

The recirculation flow type bioreactor shown in FIG. 2 was used in these studies. For pre-exposure, free microorganisms were exposed to south pole magnetic fields for 3 days prior to use in the bioreactor which contained immobilized activated sludge and phenol. Oxygen, phenol concentration and pH were measured as in Example 1. Each experimental run was 1296 hours (54 days) in length. Runs performed were:
1. Control: no magnetic on the bioreactor; bacteria not pre-exposed.
2. No magnetic field on the bioreactor; pre-exposed bacteria.
3. South magnetic pole exposure to bioreactor; pre-exposed bacteria.
4. Higher strength south magnetic pole exposure to bioreactor; pre-exposed bacteria.

Table 2 shows the results of these experimental runs. FIGS. 7 and 8 show the effect of magnetic fields on the rates of oxygen consumption which indicates that the 1500 gauss south pole magnetic field yielded the higher oxygen consumption rate of 2500 nmol/ml*hr after 15 hours into the run. FIG. 9 shows that oxygen consumption rates were higher for 1500 gauss south pole magnetic fields when compared to 3500 gauss fields.

TABLE 2

| | 1500 gauss | Time (days) | 3500 gauss | Time (days) |
| --- | --- | --- | --- | --- |
| Maximum rate of biodegradation | 25.6 ppm/hr | 11 | 14.4 ppm/hr | 4 |
| Maximum rate of oxygen consumption | 1649 nmole/ml*hr | 10 | 962 nmole/ml*hr | 5 |
| Maximum protein concentration | 2250 ug/ml | 11 | 465 ug/ml | 4 |

EXAMPLE 3

Figure 10:
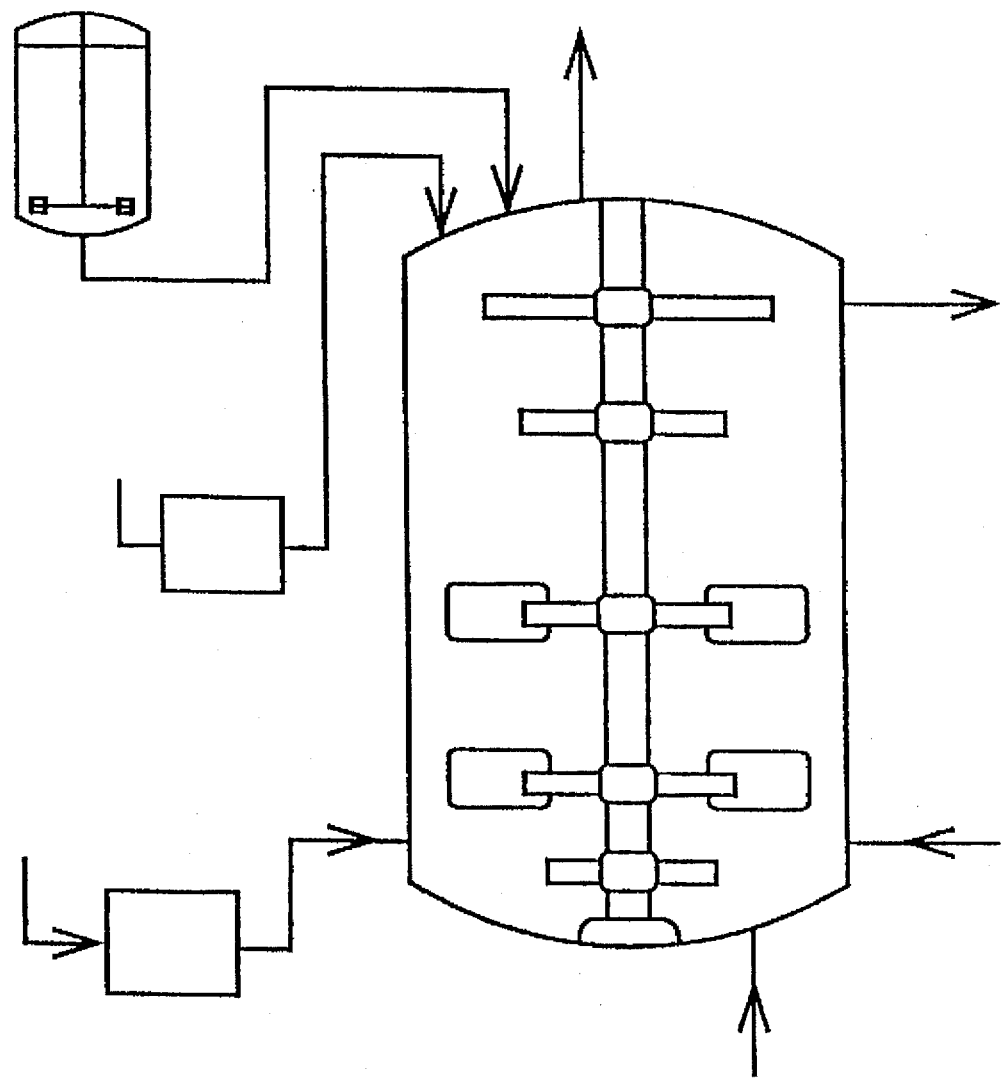
FIG. 10 is a schematic illustration of a process for producing plastic in bacteria by fermenting a carbon source.

A polyester copolymer of hydroxybutric acid and hydroxyvaleric acid (PHBV) is produced by bacteria in a reactor by fermenting a carbon source as shown in FIG. 10. When a bacteria such as Alcaligenes eutrophus is depleted of the nitrogen it requires to multiply, growth is inhibited. The carbon source, such as glucose, can then be added to the fermenter, causing the organism to make granules of polyester with the abundant carbon instead of using it to grow. The conventional process is so slow as to be economically unfeasible. The process is repeated with the exception that a south unipolar magnetic field is applied to the organism during the glucose fermenation step. The rate of fermentation will be substantially enhanced.

The effects of unipole application is further applicable in the field of biology. The application of a south magnetic field speeds up the reproduction of cells, while the north field slows reproduction.

Fermentation, a simple, anaerobic method to generate energy in the cell, is commonly used in yeast products and to produce alcholoic beverages. Carbohydrate molecules breakdown into simpler molecules such as ethyl alcohol, lactic acid, or carbon dioxide, releasing energy in the form of adenosine triphosphate (ATP). An applied south field dramatically speeds up the fermentation process. Chemostats, with their controlled environment, are ideal rapid, mass reproduction of cells, through fermentation, in combination with a unipolar magnetic field.

Further, the magnetic fields influence the growth rate of the aerobically reproduced cells. The application of a south magnetic field increases the production of enzymes without fracturing the cells. The permeability of the cell walls is increased which allows for the influx and efflux of enzymes.

The magnetic fields affect the cells either of two ways. The first is through the cell wall and would include the production and expression of proteins, such as enzymes, insulin and other hormones, interferons and antibiotics. The second is affecting the cells intracellularly and retained the affect within the cell. The appropriate magnetic field is applied for a time period and an intensity which is based on the recepient of the field, the medium and the desired end result. Examples would be many new drugs under evaluation for their effectiveness against cancer and aids.

Although research has been done on the affects of magnetism in both fermentation and other biological processes, they have used bipolar, complex or rotating fields. The instant invention relates to the consistent use of either a north or south magnetic field to produce a desired result. Thus, the cell reproduction can be decreased or increased dependent on the requirements.

Although the invention has been illustrated by the foregoing examples, it is not to be considered as being limited to the materials and processes employed therein, but rather, the invention relates to the generic area as herein before disclosed. Various modifications can be made without departing from the spirit or scope thereof.

What is claimed is:

1. The method of modifying the reproduction rate of cells by exposing said cells to north directional unipolar magnetic fields, thereby decreasing said reproduction rate.

2. The method of modifying the reproduction rate of cells by exposing said cells to south directional unipolar magnetic fields, thereby increasing said reproduction rate.

* * * * *